US008019090B1

(12) United States Patent
Agrawal et al.

(10) Patent No.: US 8,019,090 B1
(45) Date of Patent: Sep. 13, 2011

(54) ACTIVE FEEDFORWARD DISTURBANCE CONTROL SYSTEM

(75) Inventors: Brij N. Agrawal, Monterey, CA (US); Suranthiran Sugathevan, Vancouver, WA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 437 days.

(21) Appl. No.: 12/369,903

(22) Filed: Feb. 12, 2009

(51) Int. Cl.
*A61F 11/06* (2006.01)

(52) U.S. Cl. .................... 381/71.1; 381/94.1; 381/71.12

(58) Field of Classification Search ................. 381/71.1, 381/94.1, 71.12
See application file for complete search history.

(56) References Cited

U.S. PATENT DOCUMENTS 4,677,676 A * 6/1987 Eriksson .................... 381/71.11
5,206,911 A 4/1993 Eriksson et al.
5,680,337 A * 10/1997 Pedersen et al. .............. 708/322
5,715,320 A * 2/1998 Allie et al. ................. 381/71.12
5,745,580 A * 4/1998 Southward et al. .......... 381/71.1
6,097,823 A * 8/2000 Kuo .............................. 381/312
7,343,016 B2 * 3/2008 Kim ........................... 381/71.12

* cited by examiner

*Primary Examiner* — Patricia Nguyen
(74) *Attorney, Agent, or Firm* — Donald E. Lincoln; Lisa A. Norris

(57) ABSTRACT

Noise effects in a signal for driving a plant are reduced by generating a reference signal from the error signal. A signal generator generates a reference signal for input to a finite impulse response (FIR) filter. The error signal is produced by differencing the transfer function output and a disturbance signal. The error signal is input to the signal generator and to a least mean square calculator. The reference signal is input to a copy of the transfer function that outputs a modified reference signal. The modified reference signal is input to least mean square calculator. An LMS signal that updates the filter coefficients to minimize the mean square error is calculated and the LMS signal and the reference signal are input to the FIR filter with the FIR filter being arranged to process the LMS signal and the reference signal to minimize the error signal.

2 Claims, 11 Drawing Sheets

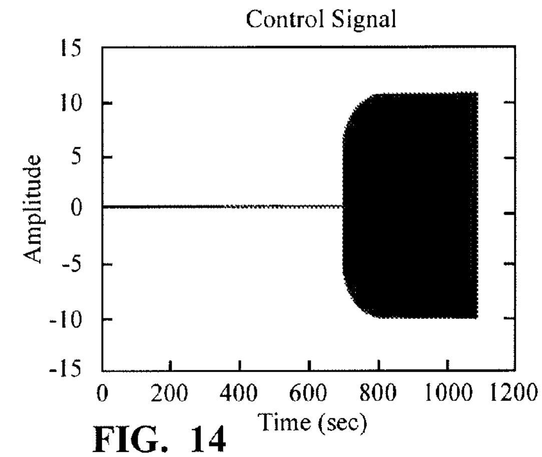
FIG. 14
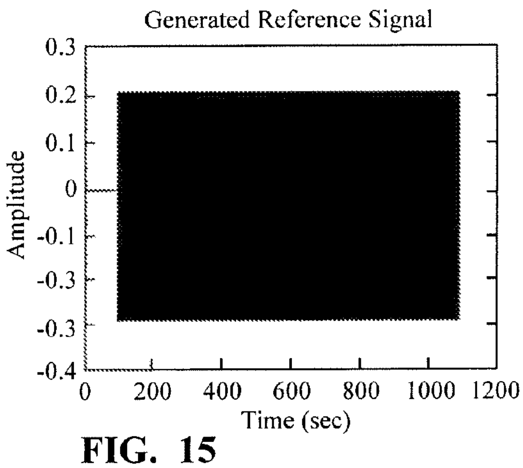
FIG. 15
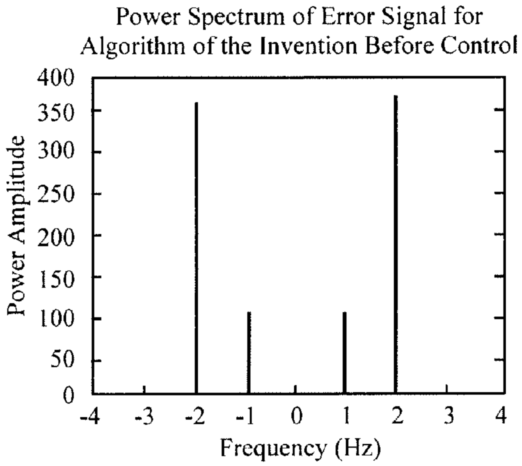
FIG. 16
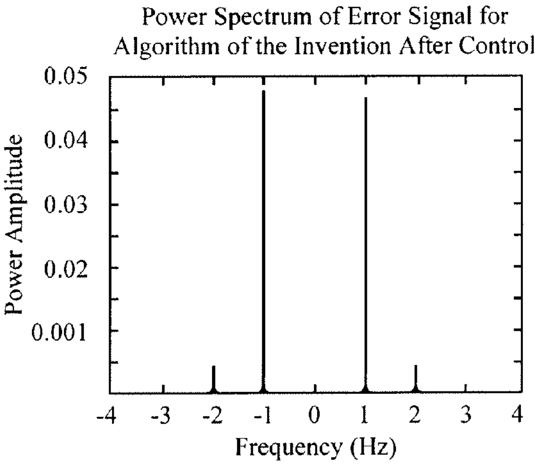
FIG. 17
FIG. 18
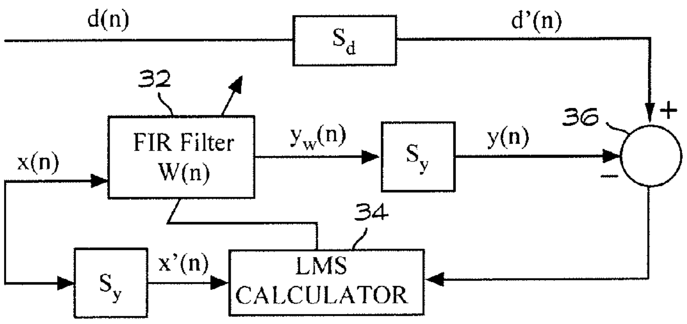

ACTIVE FEEDFORWARD DISTURBANCE CONTROL SYSTEM

BACKGROUND OF THE INVENTION

1. Field of the Invention

The invention relates generally to signal processing to reduce the effects of noise and particularly to a Least Mean Square (LMS) vibration/noise control algorithm. Still more particularly to a Least Mean Square vibration/noise control algorithm that eliminates the requirement for a reference sensor to generate a reference signal.

2. Description of the Related Art

Active noise or disturbance attenuation has been a high priority issue for many years for applications such as acoustic systems and industrial equipment. The advance of optical laser systems and their increased usage in satellites, space missions, imaging systems, communication and many military applications have established a new trend towards a more critical look at active disturbance control systems. Ever growing demands such as arc-second accuracy and nano-radian jitter require precise and efficient control systems. The growing widespread use of lasers for communications, space and military missions and the increased requirements on the specifications such as precise pointing have demanded efficient optical control methods in recent years. Unlike other communication media such as radio wave, which spreads in a spherical pattern, precision pointing and jitter control are very crucial to efficient laser communications systems. This is mainly because the presence of jitter reduces the intensity of the laser beam and causes fluctuations in the optical beam. The environmental factors such as the atmosphere and the structural interactions that cause vibrations to laser beams often add unwanted fluctuations to optical laser beams. The effect of the atmosphere on the laser beam is considered very serious because it adds broadband disturbance to optical lasers.

The control of a disturbance or noise has its origin in the areas of acoustics and structures. The use of passive systems that blanket the area with material that would absorb the noise frequencies and the use of damping components to reduce the structural vibrations are some of the commonly applied noise or vibration control techniques. Unfortunately, these techniques cannot be applied to control jitter on optical laser beams due to the time-varying characteristics of disturbances and other obvious reasons such as size and weight limitations.

Adaptive noise control algorithms have been successfully applied to reduce noise in many acoustic systems for many years. Since the noise source and the environment are time varying in general, it is often desired that an active noise control system be adaptive. Furthermore, the use of adaptive filters in the noise control systems has been proven to be low cost and very efficient. Moreover, the recent advances in signal processing and the availability of Digital Signal Processor (DSP) chips have enhanced the practicality of the adaptive filters. Adaptive filters and their applications have been widely studied by many researchers in the past. The basic idea is to design a digital filter such that its output while being passed through the system generates an antinoise component of equal amplitude and opposite phase. According to the principle of superposition, noise and antinoise components are combined to cancel each other resulting in noise elimination or reduction.

Adaptive filters are designed by minimizing an error function and can be realized as Finite Impulse Response (FIR), Infinite Impulse Response (IIR) or lattice and transform-domain filters. The most commonly used adaptive filter is the FIR filter using a Least Mean Square (LMS) algorithm. In this method, the adaptive noise cancellation is achieved through two distinct operations: 1) a digital FIR is used to perform the desired signal processing, and 2) an adaptive LMS algorithm is used to adjust the coefficients of the digital filter. An FIR filter is a digital filter that in response to a Kronecker delta input produces a response that settles to zero in a finite number of sample intervals. An Nth order FIR filter has a response to an impulse that is N+1 samples in duration. This is in contrast to IIR filters that have internal feedback and may continue to respond indefinitely. The input and output signals for an FIR filter are related by the difference equation $$y(n) = b_0x(n) + b_1x(n-1) + \ldots + b_Nx(n-N) = \sum_{i=0}^{N} b_ix(n-i),$$

where x(n) is the input signal, y(n) and $b_i$ are the filter coefficients.

A serious issue associated with the prior art implementations of the LMS algorithm for noise cancellation is the requirement of a coherent reference signal, which must be well correlated with the disturbance or noise. A common practice is to measure the disturbance or noise directly and use it as the reference signal to the LMS algorithm. A direct measurement of disturbance may not be possible always and even if it is possible, it will require that additional resources be used and eventually increase the cost of the operation or process.

SUMMARY OF THE INVENTION

Embodiments in accordance with the invention provide a new method for generating the reference signal introduced. Embodiments in accordance with the invention generate a reference signal by utilizing the characteristics of the error signal, which is the difference between the responses of the system to disturbance and the control signals. Since the error signal has the frequencies of the disturbance, processing the error signal can generate a reference signal.

In accordance with one embodiment, a signal processing method for reducing noise effects by using an error signal to generate a reference signal, a drive signal to a plant, includes: generating a reference signal x(n) with a signal generator; inputting the reference signal to a finite impulse response (FIR) filter that produces a filter output signal y(n); and producing an error signal e(n) by differencing the transfer function output and a disturbance signal d(n). In some embodiments, the method further includes inputting the error signal to the signal generator and to a least mean square calculator; inputting the reference signal to a copy of the transfer function that outputs a modified reference signal x'(n); calculating in LMS calculator filter coefficients to minimize the mean square error; and inputting the LMS output and the reference signal to the FIR filter, the FIR filter being arranged to process the LMS signal and the reference signal to minimize the error signal.

BRIEF DESCRIPTION OF THE DRAWINGS

FIG. 14 graphically illustrates a control signal used in the simulations comparing one embodiment in accordance with the invention and a standard prior art algorithm.

FIG. 15 graphically illustrates a reference signal generated in accordance with one embodiment of the invention using the error signal of FIG. 13.

FIG. 16 graphically illustrates the power spectrum of the error signal of FIG. 13 applied to one embodiment in accordance with the invention before application of the control signal of FIG. 14.

FIG. 17 graphically illustrates the power spectrum of the error signal of FIG. 13 applied to one embodiment in accordance with the invention after application of the control signal of FIG. 14.

FIG. 18 is a block diagram of a standard prior art LMS implementation that includes a reference signal measured using a sensor.

DETAILED DESCRIPTION OF THE INVENTION

Figure 1:
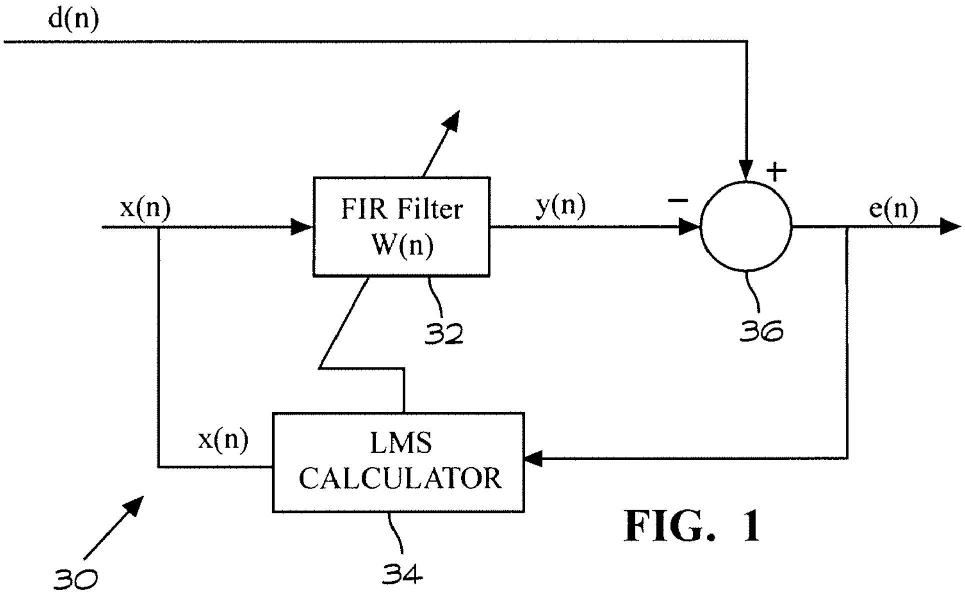
FIG. 1 is a block diagram of a basic prior art LMS structure.

FIG. 1 shows a basic prior art adaptive filter 30 without a plant. The FIR adaptive filter 30 includes an FIR filter 32 that receives a reference signal x(n). The reference signal x(n) is also input to an LMS calculator 34. A disturbance signal d(n) and the output of the FIR filter 32 are input to a summer 36. The summer 36 outputs an error signal e(n) that is the difference between the FIR filter output y(n) and the disturbance signal d(n). The error signal e(n) is fed back as a second input to the LMS calculator filter 34. The error signal e(n) and the input signal x(n) are input to the LMS calculator 34, which uses these signal inputs to calculate the filter coefficients to minimize mean square error. The result of the LMS calculation is input to the FIR filter 32.

The weights are continuously updated so that the error is progressively minimized on a sample-to-sample basis. A practical adaptive LMS algorithm uses the instantaneous squared error to estimate the mean square error The coefficients or weights of the adaptive filter 30 are adjusted by the LMS calculator 34 to minimize the mean square of the error signal e(n). Therefore, the weights of the filter coefficients are continuously updated so that the error is progressively minimized on a sample-to-sample basis. A practical adaptive LMS algorithm uses the instantaneous squared error to estimate the mean square error.

Figure 2:
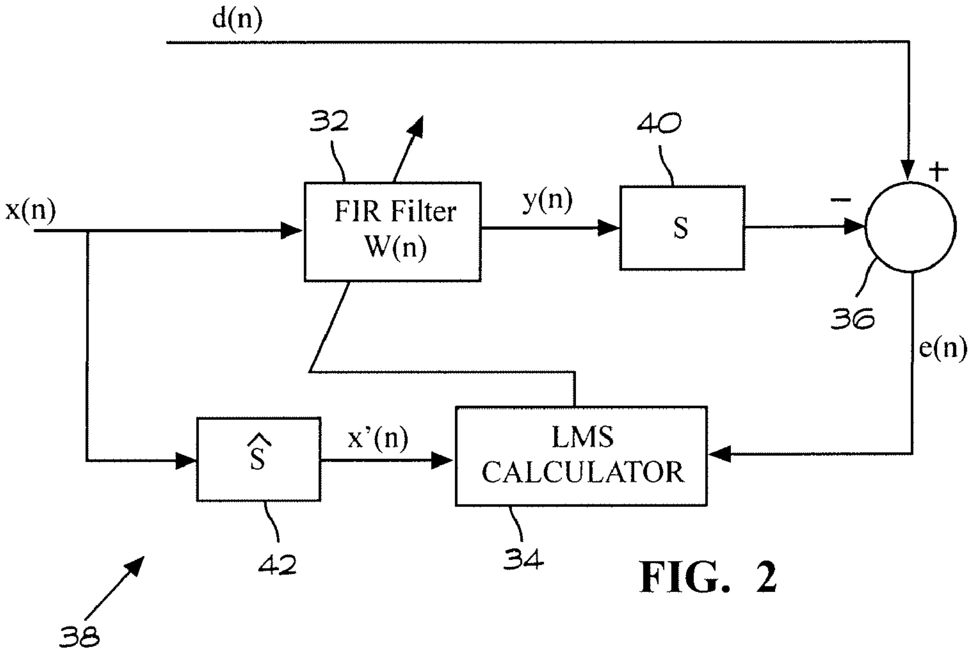
FIG. 2 is a block diagram of a modification of the LMS structure of FIG. 1.

In the arrangement shown in FIG. 1 it is assumed that the filter output can be directly added to the disturbance d(n) thus generating the error signal e(n). However, in practice, the output y(n) of the FIR filter 32 has to go through an actuator or other system device 40 before being combined with the disturbance d(n) in the summer 36. The standard LMS setup of FIG. 1 must be slightly modified for this situation as shown in FIG. 2 where S is the system transfer function and $\hat{S}$is an estimate of the system transfer function Under ideal conditions, the adaptive LMS algorithm has proven to drive the error to zero. Furthermore, it exhibits high stability and performance robustness. Another attractive feature is that precise modeling is not required in order to use it. However, a major difficulty in prior implementations of the LMS algorithm is that it requires a coherent reference signal that must be highly correlated with the disturbance or noise. In addition, the reference signal must not be contaminated by feedback from a secondary source for efficient operation. A common practice is to use a sensor, which is commonly known as a reference sensor, to measure the primary noise and use its measurement as the reference signal to the LMS algorithm. This approach may not be always practical, which may prevent the use of the LMS algorithm. Another issue is that plant noise and nonlinearity may add some other noise components, which may not be captured by the reference sensor, to the error signals. The adaptive filter may not remove these components even if it is possible to measure the disturbance and to generate a reference signal that is well correlated with the primary disturbance. Several attempts to address these issues were made in the past. A single channel feedback adaptive noise attenuation system in which a reference signal is regenerated within the system was proposed.

Figure 3:
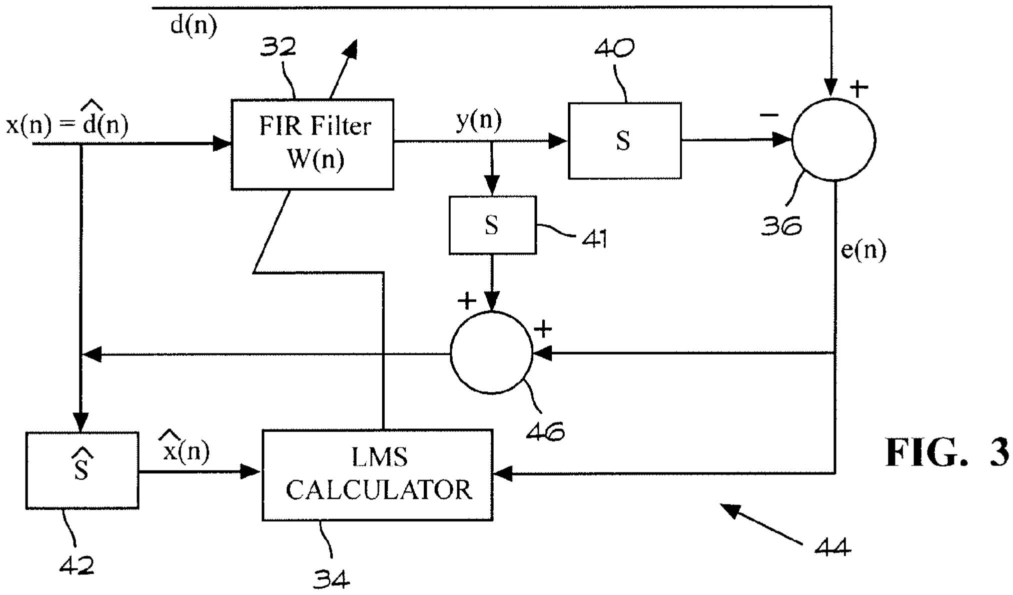
FIG. 3 is a block diagram of an LMS structure that includes an estimated reference signal.

This method was later extended to the multi-channel case. The idea behind this approach is illustrated in FIG. 3. The error signal e(n) from the summer 36 and the output y(n) from the FIR adaptive filter 32 through transfer function S are added to generate a reference signal to the LMS algorithm. It is noted that an accurate model of the plant transfer function S must be known for the efficient operation of this technique. Furthermore this method utilizes the error feedback, which in turn may introduce additional stability issues to the problem. Moreover, this feedback scheme is very sensitive to measurement noise because repeatedly feeding back this measurement noise into the system may undesirably excite the LMS algorithm, which may result in overall system instability.

This invention provides a new approach to generate the reference signal to the LMS algorithm. The novelty of this approach is that a reference signal is created by using only the spectral details of the error sensor data. As a result, the main benefit is the elimination of the reference sensor. Furthermore, it is shown that in order to generate the reference signal, it is not required to estimate the disturbance signal by combining the error signal with the filter output. These results further eliminate the requirement of the accurate online modeling of the system. Similar or better performance is attainable using the method according to the present invention by simply analyzing the error signal and using it to generate a suitable reference signal. Another improvement is that the invention utilizes a feedforward control technique; and therefore, it is guaranteed to provide large stability bounds. Furthermore, a unique feature of the invention is that it can also be used to attenuate measurement noise. Since the reference signal is generated using the error signal, this method is designed to handle the primary disturbance as well as the measurement or process noise.

The present invention is intended for applications with narrow band disturbances. Attenuation of broadband or random disturbance presents issues not addressed by this invention. The methodology of the present invention is validated through the computer simulations and the experiments performed on an optical laser test bed.

Figure 4:
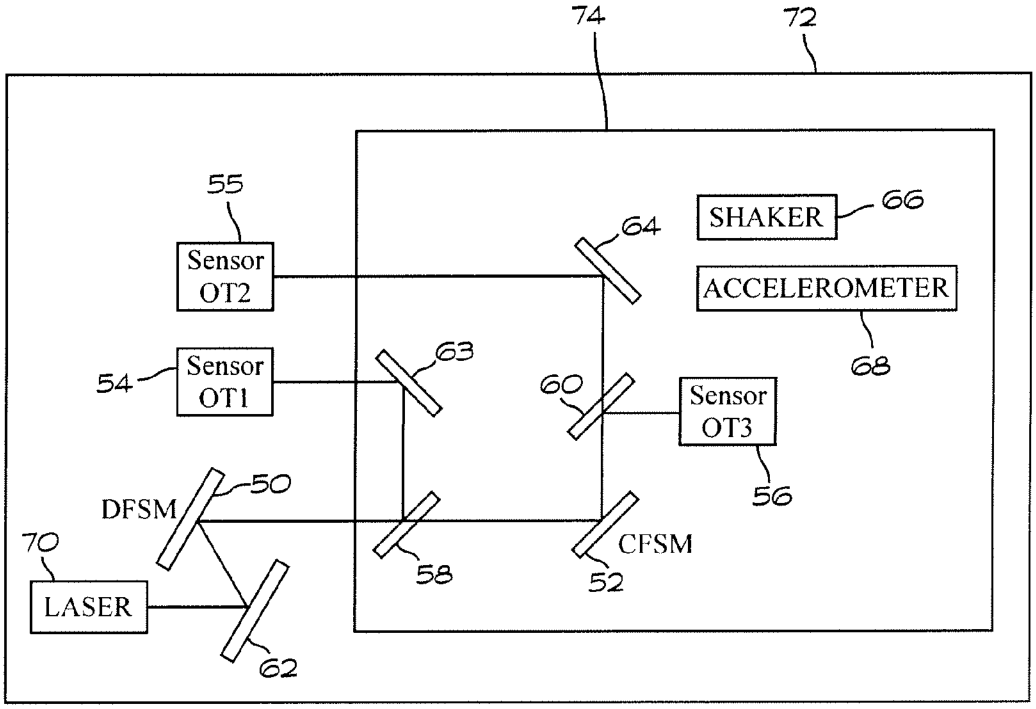
FIG. 4 is schematic diagram of optical laser test bed.
Figure 5:
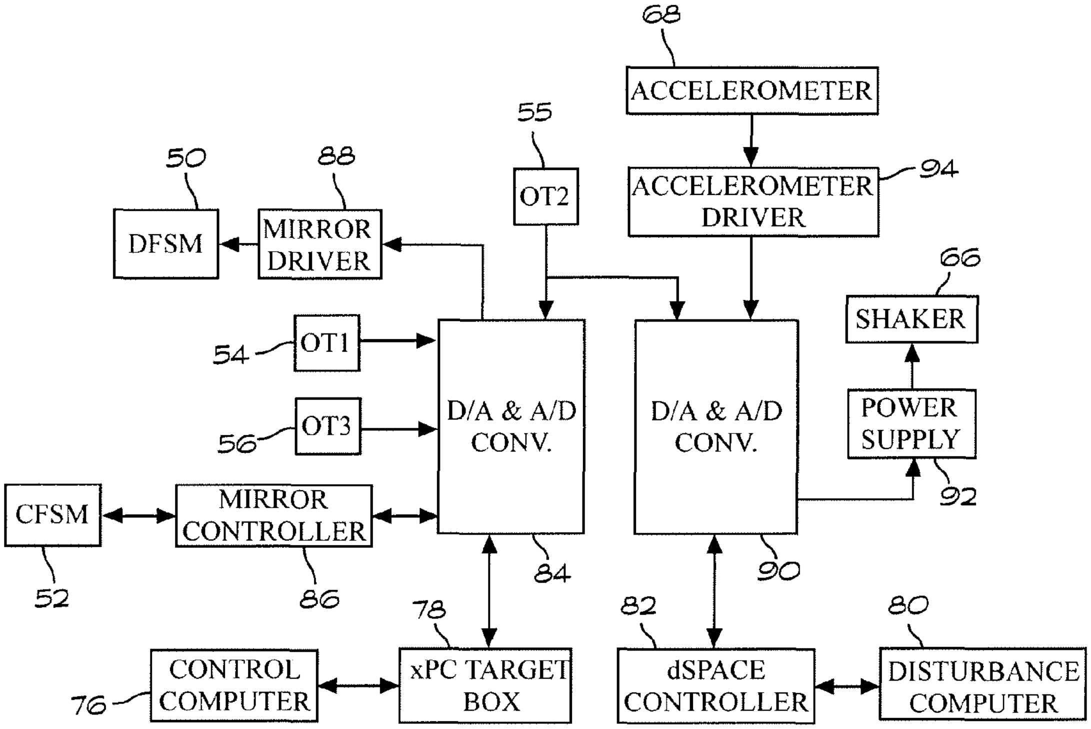
FIG. 5 is a signal flow diagram for the test bed of FIG. 4.

The optical laser test bed 72 is schematically shown in FIG. 4. FIG. 5 is a signal flow diagram of the test bed 72. The test bed 72 includes a Disturbance Injection Fast Steering Mirror (DFSM) 50, a Control Fast Steering Mirror (CFSM) 52, three On-Trak position-sensing devices 54-56, two 80/20 beam splitters 58 and 60, three optical folding mirrors 62-64, a shaker 66, an accelerometer 68, and a laser source 70. The components are mounted on an optical bench 72, which is floated to isolate the external disturbances. The beam splitter 58 and 60, the mirror 52, 63 and 64, the sensor 56, the shaker 66 and the accelerometer 68 are mounted on a Newport vibration isolation platform 74.

Folding mirror 62 is used to divert the laser beam to the DFSM 50, which injects the user-defined disturbance to the laser beam. The corrupted laser beam then travels through the 80/20 beam splitter 58, which splits the laser beam into two separate beams with one beam being sent through the control mirror CFSM 52 while the other is reflected onto the folding mirror 63, which directs the beam to the sensor 54 where the position of the laser beam is measured.

As shown in FIG. 5, the control mirror CFSM 52 is connected to a mirror controller 86 that is also connected to a D/A and A/D converter module 84. A control computer 76 has its output connected to an xPC target box 78 that is in turn connected to the module 84. The control mirror 52 receives control commands from the control computer 76 through the xPC target box 78 and provides the corrective actions to the laser beam while it is being passed through. The laser beam is then sent through the second beam splitter 60. One part of the beam is measured by the sensor 56, and the other part is diverted by folding mirror 64 to the sensor 55 where the X and Y positions of the laser beam are measured again. The shaker 66 is used to vibrate the Newport platform 74 in the x, y and z directions to add another form of disturbance to the laser. An accelerometer 68 attached to the Newport platform 74 is used to study the response of the platform 74. The DFSM mirror 50 is connected to a mirror driver 88 that is also connected to the module 84. As shown in FIG. 5, the mirror DFSM 50 is also controlled by the control computer 76 through the xPC Target Box 78. The pointing and jitter control algorithms are coded in Matlab/Simulink environment and are implemented on the control computer 76.

A disturbance computer 80 has its output connected to a dspace controller 82 that is also connected to a D/A and A/D module 90. A power supply 92 connected to the module 90 provides electric power to the shaker 66, which is controlled by the disturbance computer 80. An accelerometer driver 94 is connected between the accelerometer 68 and the module 90 so that the accelerometer 68 is controlled by the disturbance computer 80.

Even though the optical laser beam pointing system is a two-input-two-output system, the experiments revealed that the interactions among the loops (X and Y axes) are negligible and the system can be considered as two independent single-input-single-output systems. Therefore, the controllers for the X and Y-axes are designed independently. In order to avoid the repetition of similar material, only the results of the X-axis design are presented.

Figure 6:
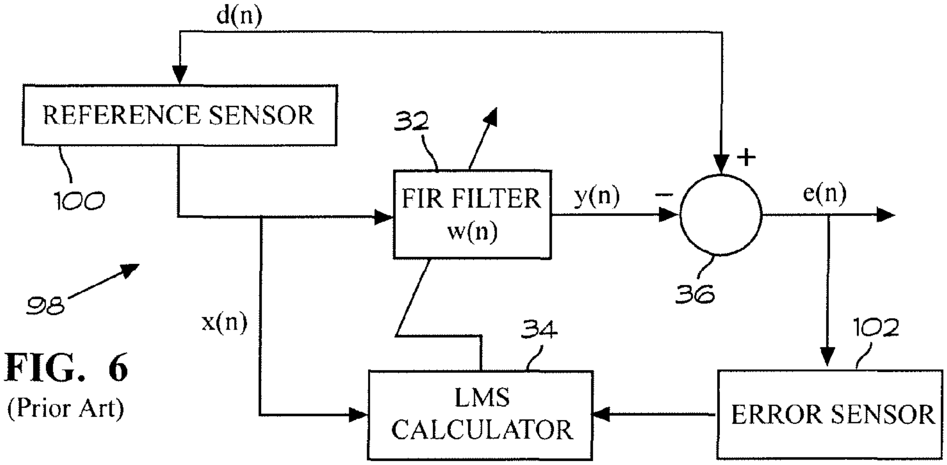
FIG. 6 (Prior Art)
FIG. 6 is a block diagram of a standard LMS implementation for narrow band disturbance rejection.

FIG. 6 shows the standard LMS implementation for narrowband disturbance rejection. A reference sensor 100 is used to generate a reference signal to the LMS calculator 34, and an error sensor 102 is used to measure the error signal, which is another input to the LMS calculator 34. The relation between the filter output y(n) and the reference signal x(n) may be expressed as $$y(n)=w^T x(n). \tag{1}$$

The error signal at time instant n is determined by $$e(n)=d(n)-y(n). \tag{2}$$

The mean squared error (MSE) $\xi(n)$ of the error signal is chosen as the performance measure where $$\begin{aligned}\xi(n) &= E\{e^2(n)\} && (3\\ &= E\{d^2(n)\} - 2E\{d(n)x(n)\} + w^T E\{x(n)x^T(n)\}w && (4\\ &= E\{d^2(n)\} - 2p^T w + w^T Rw && (5\end{aligned}$$

where p represents the cross-correlation between d and x and R represents input correlation and brackets { } denoting the expected value.

The method of steepest descent is used to find a coefficient that minimizes the performance measure $\xi(n)$ defined by Equation (3). In order to use the method of steepest descent, the gradient of $\xi$ is derived $$\nabla\xi(n)=-2p+2Rw(n). \tag{6}$$

The following LMS algorithm 34 determines the FIR filter w(n):

$$w(n+1)=w(n)+\mu(p-Rw(n)) \tag{7}$$

with $\mu$ being the twice the step size.

The MSE of the error signal is estimated to be $$\xi(n)=e^2(n) \tag{8}$$

The gradient of $\xi(n)$ is given by $$\begin{aligned}\nabla\xi(n) &= 2\nabla e(n)e(n) && (9)\\ &= -2x(n)e(n) && (10)\end{aligned}$$

The LMS algorithm 34 then becomes $$w(n+1)=w(n)+\mu x(n)e(n) \tag{11}$$

It is noted that in order to use the above algorithm, it is required to have two inputs: (1) a reference signal, which must be highly correlated with the disturbance and (2) an error signal. As shown in FIG. 6, two sensors 100 and 102 are required to supply these two inputs. In practice, it is often possible to measure the error signal. However, the measurement of disturbance may be tedious, if not impossible. This invention is focused on avoiding the difficulty of measuring the reference signal and provides a new approach that eliminates the use of the reference sensor but still produces the similar results.

The reference sensor 100 is not needed to implement the LMS algorithm. Since the error signal contains the frequencies of the disturbance, it is possible to understand the behavior and the frequency content of the disturbance signal by analyzing the error signal. Having obtained this information, a reference signal can be generated by using the error sensor data alone.

Figure 7:
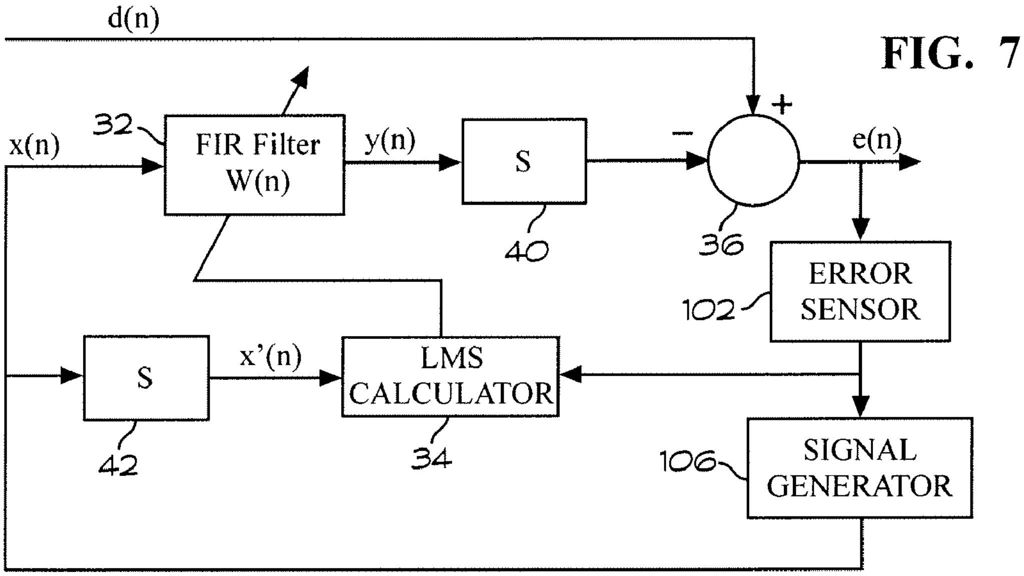
FIG. 7 is a block diagram of an LMS implementation in accordance with one embodiment.

FIG. 7 shows an adaptive filter 104 according to the present invention. This approach is valid because the LMS algorithm does not require the amplitude and phase of the disturbance signal, but it requires only the frequency content of the disturbance. Therefore, it is noted that a reference sensor is not always necessary in order to implement the LMS algorithm. As will be shown later, similar or better disturbance attenuation can be attained using one error sensor 102 and a signal generator 106. Using the reference sensor 100 to generate the reference signal solves the primary disturbance attenuation problem, and it does not provide a solution to suppress other secondary noise components such as measurement noise, process noise, and foreign frequency components due to system nonlinearity. It will be shown that the use of error sensor data to generate the reference signal has the ability to bundle all of the above noise components in addition to the primary disturbance.

The function of the signal generator 106 shown in FIG. 7 and the main steps involved in implementing the LMS algorithm without a reference sensor can be summarized as:

Step 1: Start the experiment and wait for a few seconds until the transients die out.

Step 2: Capture the error sensor data for a short period of time that is sufficient to record all the spectral details.

Figure 8:
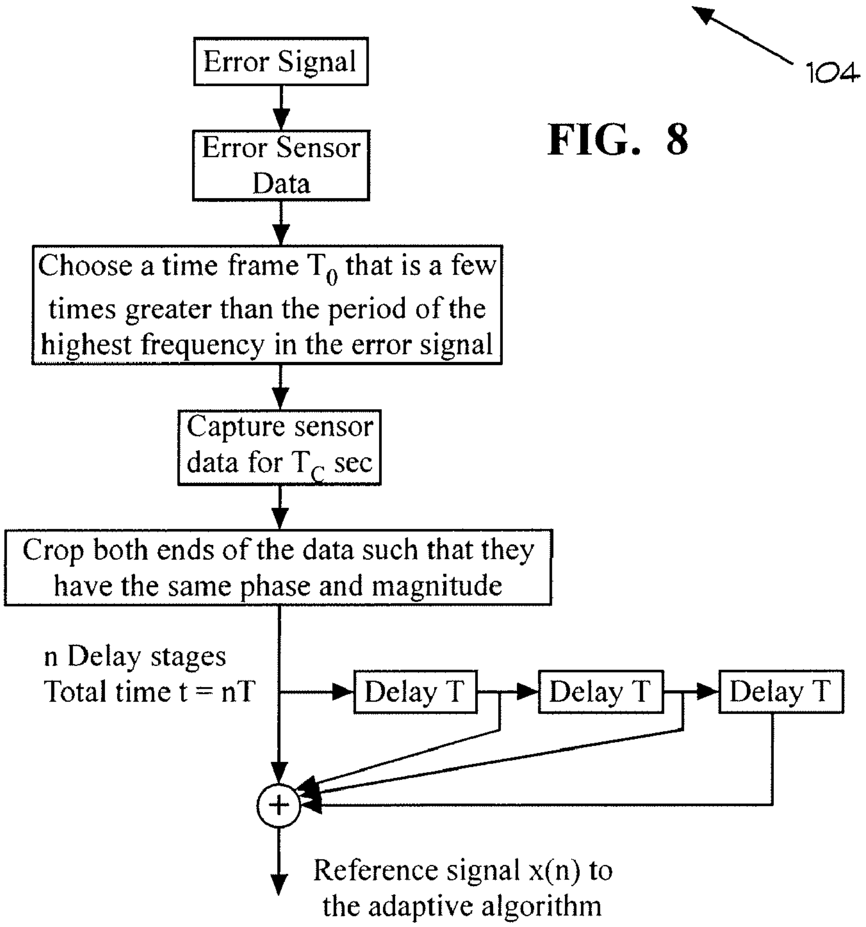
FIG. 8 is a logic diagram for a first implementation of step 3 of the algorithm used with FIG. 7 in accordance with one embodiment.
Figure 9:
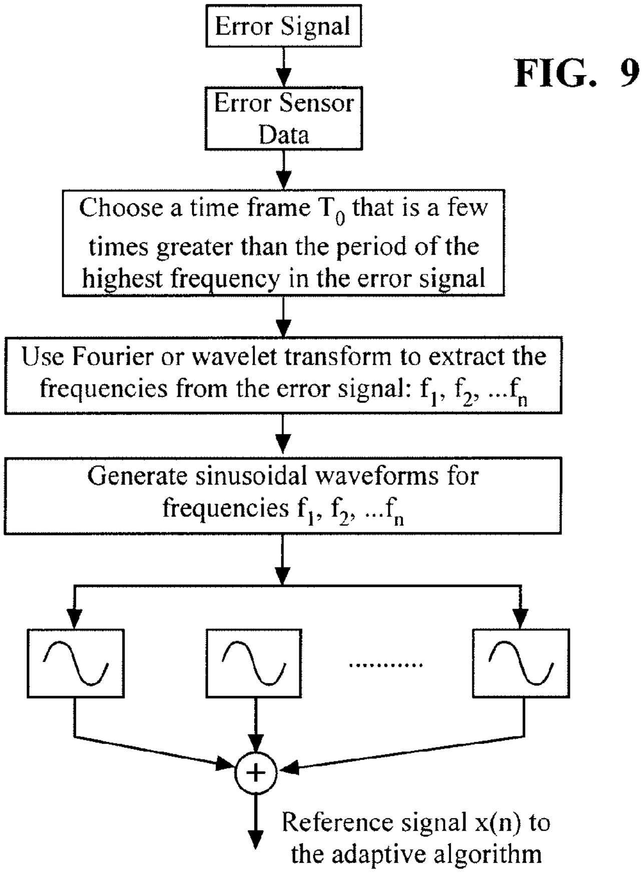
FIG. 9 is a logic diagram for a second implementation of step 3 of the algorithm used with FIG. 7 in accordance with one embodiment.

Step 3: Generate the reference signal by channeling the captured error sensor data repeatedly while ensuring the continuity of data (FIG. 8). Alternatively, the frequency content of the captured error sensor data may be estimated and sine wave generators may be used to create the reference signal that contains the frequencies of the error signal (FIG. 9).

Figure 10:
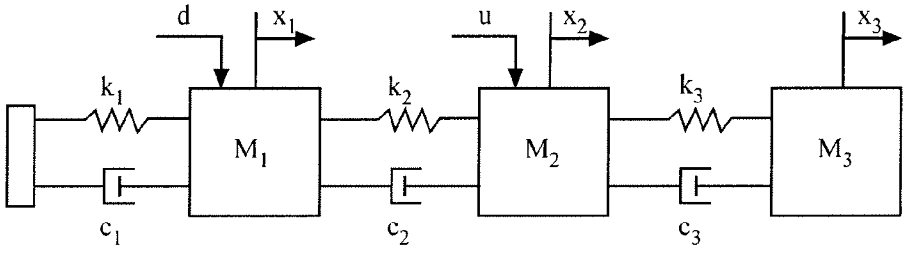
FIG. 10 illustrates a mass and spring system.

In order to test and validate the algorithm according to the present invention, a three-degree of freedom mass and spring system as shown in FIG. 10 was simulated in a Matlab platform. Let $X_3$ be the displacement of mass $M_3$ from the initial stable position. Mass $M_1$ is subject to an external disturbance d, mass $M_2$ is subjected to control u. The objective is to minimize $X_3$ using the control command u. The displacement $X_3$ is related to the disturbance d and the control input u by $$x_3=S_d d-S_y u$$

where $S_d$ is the transfer function relating $x_3$ and d and $S_y$ is the transfer function relating $x_3$ and u.

Figure 11:
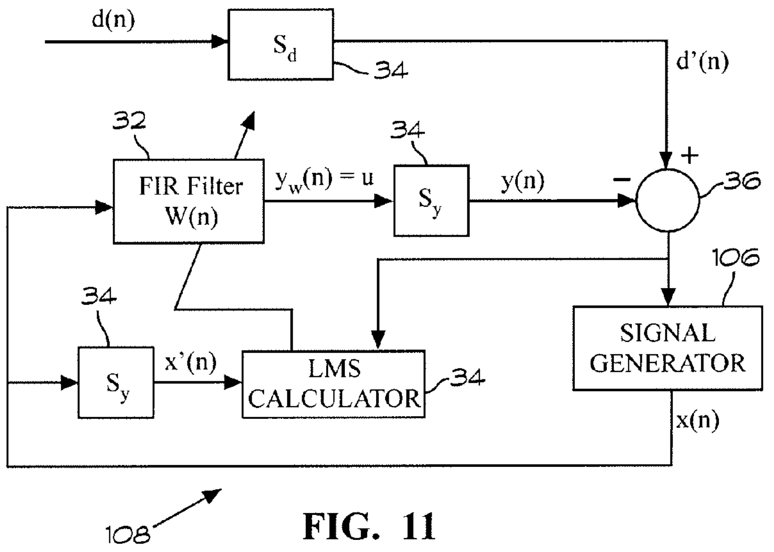
FIG. 11 is a block diagram of an alternate LMS implementation in accordance with another embodiment.

FIG. 11 illustrates an adaptive filter 108 modified to accommodate transfer functions $S_d$ and $S_y$ in the setup. A disturbance signal with frequencies 1 and 2 Hz was used for the computer experiments. The simulation was run for 1100 seconds, and the adaptive controller was set to deliver its commands at the 700th second of the simulation. This is done in order to study the effects of the control commands before and after the control. As explained in the previous section, capturing the error signal and extracting its frequency content generate the reference signal for the error signal.

Figure 12:
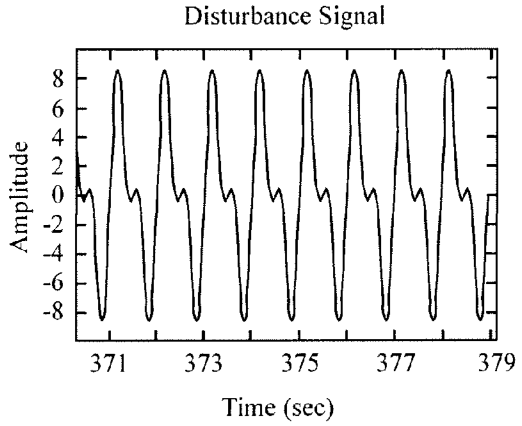
FIG. 12 graphically illustrates a disturbance signal used in simulations comparing one embodiment in accordance with the invention and a standard prior art algorithm.
Figure 13:
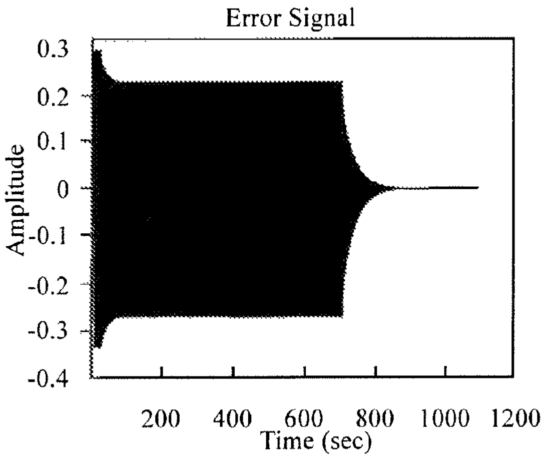
FIG. 13 graphically illustrates an error signal that results from the disturbance signal of FIG. 12.

The disturbance signal used for this simulation is shown in FIG. 12. The error signal is shown in FIG. 13. The control commands are shown in FIG. 14, and the generated reference signal is shown in FIG. 15. The power spectrums of the error signal before and after control are shown in FIGS. 16 and 17, respectively.

Figure 19:
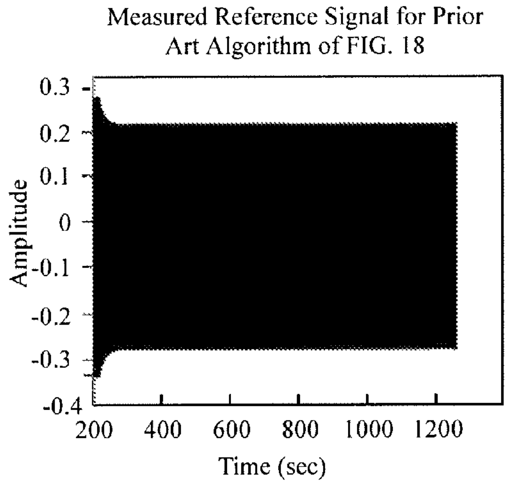
FIG. 19 graphically illustrates a measured reference signal for the prior art LMS implementation of FIG. 18.
Figure 20:
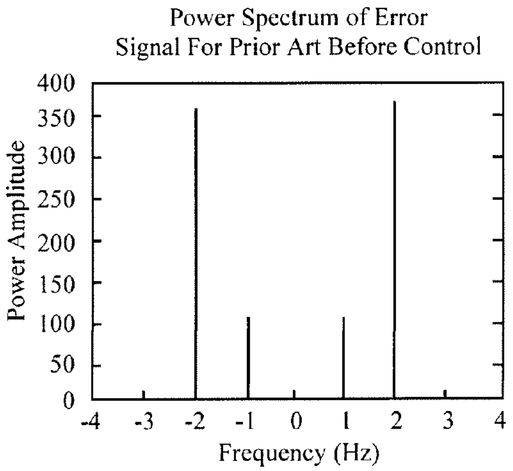
FIG. 20 graphically illustrates the power spectrum of the error signal of FIG. 13 before application of the control signal of FIG. 14.
Figure 21:
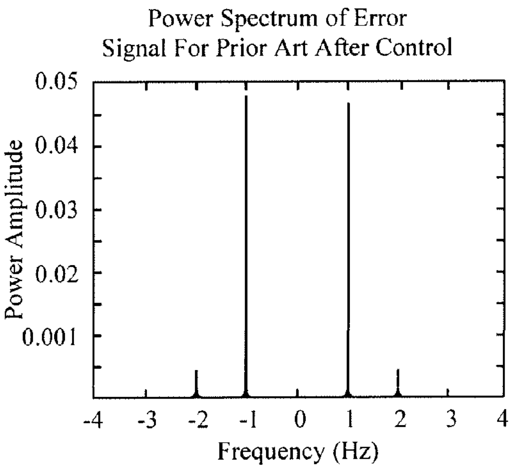
FIG. 21 graphically illustrates the power spectrum of the error signal of FIG. 13 after application of the control signal of FIG. 14 in accordance with one embodiment.

To compare the results obtained using the proposed LMS setup, another set of simulations was run, this time, using the standard LMS setup standard LMS setup, shown in FIG. 18, where reference signal is measured using a sensor. The same disturbance signal used in the first simulation is used again in the standard LMS setup. The measured reference signal is shown in FIG. 19. The power spectrums of the error signal before and after the control are shown in FIGS. 20 and 21 respectively. Comparing the error signals and power spectrums before and after the control in both cases reveals that the LMS algorithm used in the present invention and the standard LMS algorithm produce the same results. It is worth mentioning again that the proposed algorithm does not require a reference sensor while the standard algorithm requires one to measure the disturbance.

Figure 22:
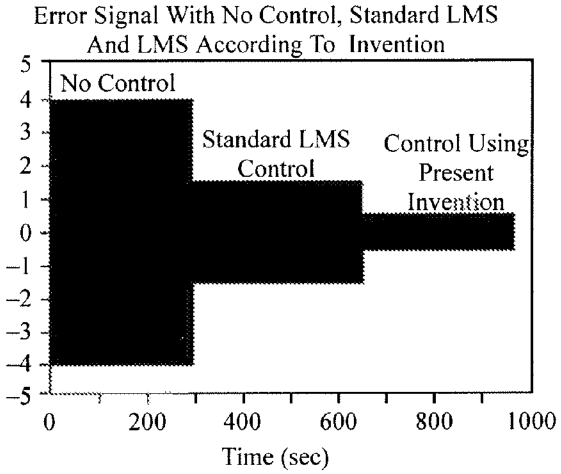
FIG. 22 shows simulation results performed with a nonlinear plant.

FIG. 22 shows the simulation results performed with a nonlinear plant $y=x^3$. For the first 300 seconds, the simulation was run without any control, and the standard LMS controller was activated at the 300th second. The standard LMS controller was deactivated at the 650th second, and the LMS controller according to the present invention was set to deliver its control commands immediately. It is clear that the controller according to the present invention removes some of the distortion caused by system nonlinearity.

The algorithm was implemented on the optical laser test bed 72 shown in FIG. 4 to test and validate its performance in attenuating the optical laser jitter. Two experiments were performed with two different disturbance signals. As described previously herein, the disturbance is injected to the laser beam using the DFSM 50; and the control commands are delivered through CFSM 52. The laser beam position on the chart of sensor 55 in X direction is the output for the experiment.

Figure 23:
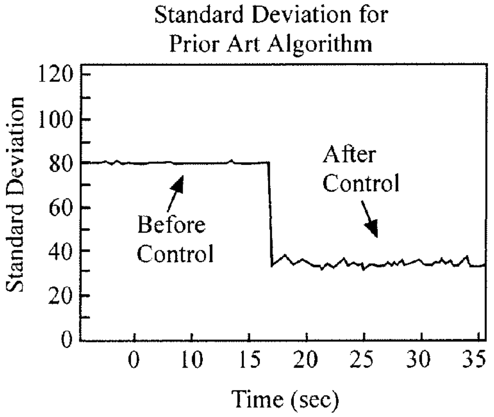
FIG. 23 graphically illustrates the standard deviation in the error obtained using the prior art of FIG. 18 before and after application of a control signal.
Figure 24:
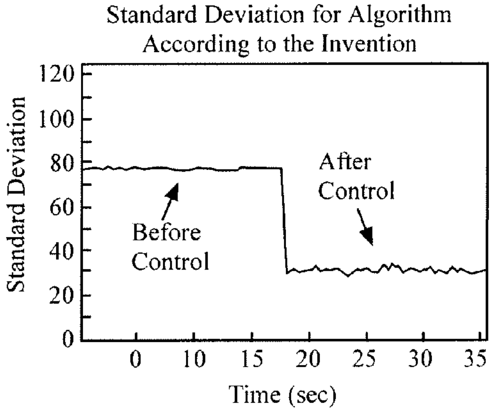
FIG. 24 graphically illustrates the standard deviation in the error obtained using the algorithm in accordance with one embodiment of the invention before and after application of a control.
Figure 25:
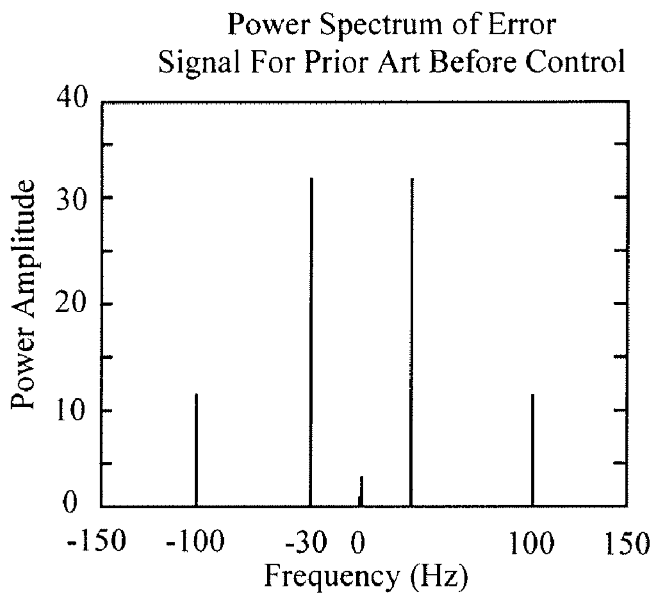
FIG. 25 graphically illustrates the power spectrum of the error signal for the prior art algorithm before application of a control signal.
Figure 26:
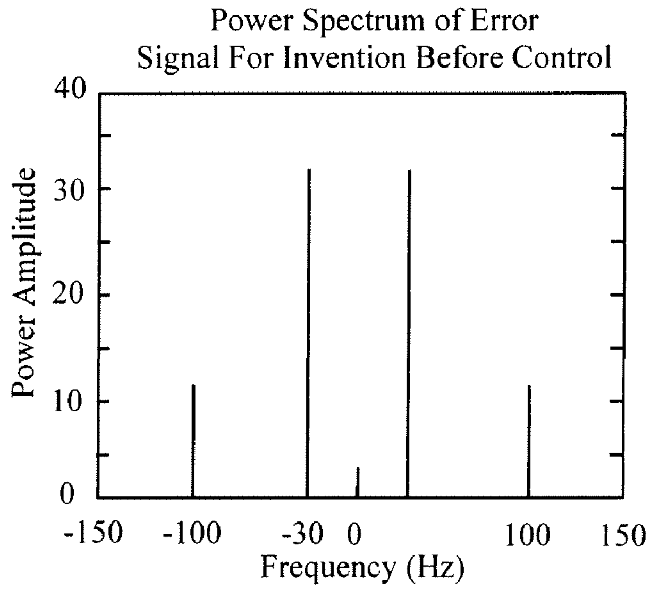
FIG. 26 graphically illustrates the power spectrum of the error signal in accordance with one embodiment before application of a control signal.
Figure 27:
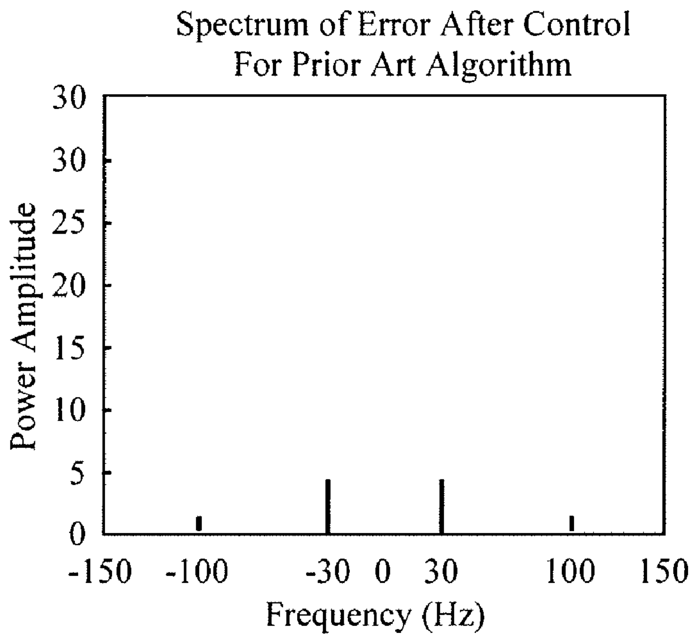
FIG. 27 graphically illustrates the spectrum of the error signal using the prior art algorithm with a control signal.
Figure 28:
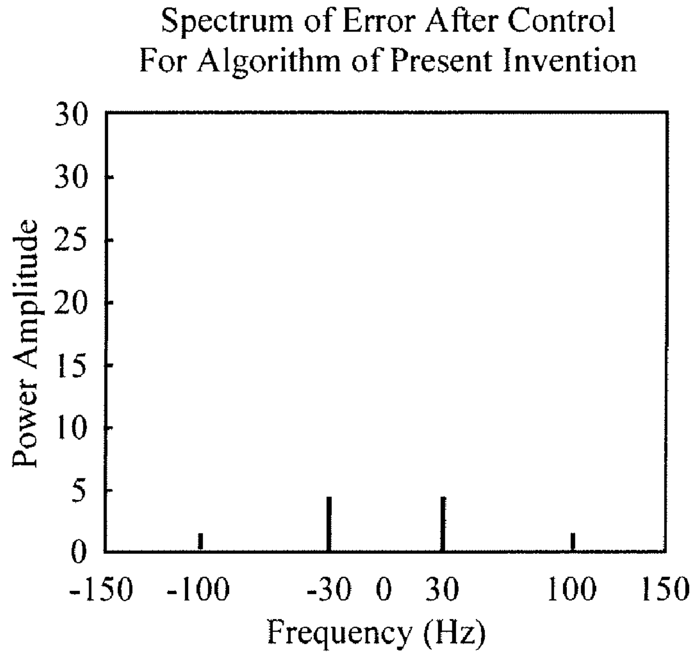
FIG. 28 graphically illustrates the spectrum of the error signal using the algorithm in accordance with one embodiment with a control signal.

In order to demonstrate the performance of the invention compared to the standard algorithm, two experiments were performed. In the first experiment, the standard adaptive algorithm was used to control the jitter, whereas in the second experiment, the algorithm according to the present invention is utilized to do the same. Both were carried out with the same disturbance. A disturbance with frequencies 30 Hz and 100 Hz is generated and injected into the laser beam. The controller is set to deliver its commands at the 16th second of the experimental run. The standard deviation plots of the laser beam position obtained with the standard and the proposed algorithms are shown in FIGS. 23 and 24 respectively. FIGS. 25 and 26 compare the power spectrums of the laser beam position obtained using the standard and modified algorithms before the controller is activated. The power spectrums of the laser beam position obtained using two different algorithms with the controller being active are compared in FIGS. 27 and 28. The experiments are stopped a few seconds after activating the controller. Further disturbance attenuation is possible if experiments are allowed to run for longer periods. It is observed that the results produced by the proposed method are exactly the same as those obtained with the standard setup. The main difference is that the proposed setup does not use a reference sensor to measure the disturbance. This implies that similar results can be obtained using less resources and a much simpler algorithm.

Even though the primary concern is to attenuate the disturbance, it is often necessary to attenuate other secondary noise components such as process noise and other foreign components due to system nonlinearity. Since the error signal contains all of these components in addition to the primary disturbance, the information about all the unwanted frequency components are readily available by simply processing the error sensor data.

Although this description of the invention is directed to treating jitter problems in laser communication systems, the method according to the present invention is generic and can be used to solve disturbance or noise problems in almost any environment or platform. While jitter remains a serious issue in laser communications, vibration control in large machineries, noise control in acoustic systems and microphones and jitter control in satellites and space systems are some of other important applications. It is expected the present invention will simplify the controller implementation drastically and also save resources and money.

What is claimed is:

1. A signal processing method for reducing noise effects by using an error signal to generate a reference signal to compensate for an error signal input to drive signal to a plant, comprising the steps of:

generating a reference signal x(n) with a signal generator;

inputting the reference signal to a finite impulse response (FIR) filter that produces a filter output signal y(n);

producing an error signal e(n) by differencing the transfer function output and a disturbance signal d(n);

inputting the error signal to the signal generator and to a least mean square calculator;

inputting the reference signal to a copy of the transfer function that outputs a modified reference signal x'(n);

calculating an LMS signal that is filter coefficients to minimize mean square error signal; and inputting the LMS signal and the reference signal to the FIR filter, the FIR filter being arranged to process the LMS signal and the reference signal to minimize the error signal.

2. An adaptive filter for an active noise cancellation system, comprising:

a signal generator arranged to provide a reference signal;

a finite impulse response (FIR) filter that is connected to the signal generator to receive the reference signal therefrom and arranged to provide a filter output signal y(n);

a model of a system having a system transfer function arranged to receive the filter output signal;

a summer arranged to produce an error signal e(n) by differencing the transfer function output and a disturbance signal d(n) with the error signal being input to the signal generator;

a copy of the system model connected to the signal generator to receive the reference signal therefrom and output a modified reference signal; and a least mean square calculator connected to the summer to receive the error signal therefrom and also connected to the copy of the system model to receive the modified reference signal therefrom, the least mean square calculator being arranged to calculate an LMS signal that updates coefficients of FIR filter to minimize mean square error to input to the FIR filter, the FIR filter being arranged to adjust the filter output signal y(n) such that the error signal e(n) is minimized.

* * * * *